(12) United States Patent
Hu et al.

(10) Patent No.: US 8,232,363 B2
(45) Date of Patent: Jul. 31, 2012

(54) SILICONE CONTAINING POLYMERIC MATERIALS

(75) Inventors: Can B. Hu, Irvine, CA (US); Thuy B. Mai, Anaheim, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 863 days.

(21) Appl. No.: 11/963,351

(22) Filed: Dec. 21, 2007

(65) Prior Publication Data
US 2009/0163602 A1   Jun. 25, 2009

(51) Int. Cl.
*C08L 83/07* (2006.01)
(52) U.S. Cl. .......................................... 528/32; 525/474
(58) Field of Classification Search .................. 525/474; 528/32
See application file for complete search history.

(56) References Cited

U.S. PATENT DOCUMENTS

| | | | |
|---|---|---|---|
| 4,647,282 A | 3/1987 | Fedorov et al. | |
| 4,742,142 A * | 5/1988 | Shimizu et al. | 528/15 |
| 5,217,491 A | 6/1993 | Vanderbilt | |
| 5,326,506 A | 7/1994 | Vanderbilt | |
| 5,374,663 A | 12/1994 | Daicho et al. | |
| 5,444,106 A * | 8/1995 | Zhou et al. | 523/107 |
| 5,528,322 A | 6/1996 | Jinkerson | |
| 5,543,504 A | 8/1996 | Jinkerson | |
| 5,662,707 A | 9/1997 | Jinkerson | |
| 6,277,940 B1 | 8/2001 | Niwa et al. | |
| 6,310,215 B1 | 10/2001 | Iwamoto | |
| 6,326,448 B1 | 12/2001 | Ojio et al. | |
| 6,361,561 B1 | 3/2002 | Huo | |
| 6,432,137 B1 | 8/2002 | Nanushyan et al. | |
| 6,613,343 B2 | 9/2003 | Dillingham et al. | |
| 6,638,305 B2 * | 10/2003 | Laguette | 623/6.37 |
| 6,805,712 B2 | 10/2004 | Lai et al. | |
| 7,071,244 B2 | 7/2006 | Liao | |
| 2002/0071856 A1 | 6/2002 | Dillingham et al. | |
| 2004/0111151 A1 | 6/2004 | Paul et al. | |
| 2005/0038219 A1 | 2/2005 | Lai et al. | |
| 2005/0070626 A1 | 3/2005 | Lowery | |
| 2006/0106458 A1 | 5/2006 | Jason et al. | |
| 2008/0161913 A1 | 7/2008 | Brady et al. | |
| 2008/0161914 A1 | 7/2008 | Brady et al. | |
| 2009/0088839 A1 | 4/2009 | Hu et al. | |
| 2009/0164009 A1 | 6/2009 | Hu et al. | |

FOREIGN PATENT DOCUMENTS

| | | |
|---|---|---|
| FR | 2779940 | 12/1999 |
| WO | WO 2005/055875 | 6/2005 |
| WO | WO 2005/066662 | 7/2005 |
| WO | WO2008108524 A1 | 9/2008 |
| WO | WO 2009/045902 | 4/2009 |
| WO | WO 2009/085996 | 7/2009 |
| WO | WO 2010/027519 | 3/2010 |

OTHER PUBLICATIONS

International Preliminary Report on Patentability and Written Opinion of PCT/US2008/087506, Jun. 22, 2010.
International Search Report of PCT/US09/030113, Mar. 23, 2009.
International Search Report of PCT/US2008/087506, Mar. 20, 2009.

\* cited by examiner

*Primary Examiner* — Kuo-Liang Peng
(74) *Attorney, Agent, or Firm* — Abbott Medical Optics Inc.

(57) ABSTRACT

A polymeric material with a variable modulus of elasticity is described herein. The polymeric material described herein is useful for forming implantable medical devices (e.g. ophthalmic lenses, breast implants, and body augmentation devices). In addition, medical devices formed from the polymer material can be used to controllably release a therapeutic agent. Also, the polymeric material may be used to prepare topical compositions or other applications or devices where control of a mechanical property such as material modulus is important.

5 Claims, No Drawings

SILICONE CONTAINING POLYMERIC MATERIALS

FIELD OF THE INVENTION

Disclosed herein are polymeric materials having an average of more than two terminal vinyl groups.

BACKGROUND OF THE INVENTION

The use of polymeric materials for medical devices is an area where vast improvements in polymeric materials have evolved and are still evolving. Physical properties of these polymers can be fine tuned for use in different environments or to behave in a predictable manner. Polymers for use in fabricating IOLs need to be adapted allowing for smaller incisions during implantation.

In addition to polymers with physical properties adapted for use in the optic region, polymeric material can be adapted for various applications elsewhere. Various medical devices other than optic implants can incorporate elastomeric polymeric material, for example, implantable medical device coatings, breast implants, prosthetic joins and other body augmentation implants. These types of applications each require polymeric material that may be vastly different from another. The ability of a skilled artisan is necessary to fine tune the physical properties of the polymers.

In addition to medical devices and medical device coatings, polymeric material can be incorporated into topical formulations. A low degree of polymerization can be used, for example, to form a more liquid polymeric material which can be useful in such formulations as eye drops or hair sprays. Increasing the degree of polymerization can cause the polymer to become more viscous wherein the polymer may be useful in skin creams or lotions. The degree of polymerization can be tailored for the appropriate application and various other variations are possible.

In the area of ophthalmic devices, IOLs have been designed for ever smaller incisions in the eye. Elastomeric IOLs are typically implanted using inserters to roll or fold the IOL, insert the IOL into the capsular sac, and then allow the IOL to unfold once inside. Occasionally, the fold of the IOL before insertion may result in permanent deformation, which adversely affected the implant's optical qualities. Further, while foldable IOLs have eliminated the need for the large incision, foldable IOLs are not without drawbacks. In particular, both non-deformable and foldable IOLs are susceptible to mechanical dislocation resulting in damage to the corneal endothelium.

Another approach to small incision IOL implantation uses an elastomeric polymer that becomes pliable when heated to body temperature or slightly above. Specifically, the IOL is made pliable and is deformed along at least one axis, reducing its size for subsequent insertion through a small incision. The IOL is then cooled to retain the modified shape. The cooled IOL is inserted into the capsular sac and the natural body temperature warms the IOL at which point it returns to its original shape. The primary drawback to this type of thermoplastic IOL is the limited number of polymers that meet the exacting needs of this approach. Most polymers are composed of polymethylacyrlate which have solid-elastomeric transition temperatures above 100° C. Modifications of the polymer substrate require the use of plasticizers that may eventually leach into the eye causing harmful effects.

Dehydrated hydrogels have also been used with small incision techniques. Hydrogel IOLs are dehydrated before insertion and naturally rehydrated once inside the capsular sac. However, once fully rehydrated the polymer structure is notoriously weak due to the large amount of water absorbed. The typical dehydrated hydrogel's diameter will expand from 3 mm to 6 mm resulting in an IOL that is 85% water. At this water concentration the refractive index (RI) drops to about 1.36, which is unacceptable for an IOL since lower RI materials require the optic to be thicker to achieve a given optical power.

Modern acrylate IOLs generally possess excellent mechanical properties such as foldability, tear resistance and physical strength. Acrylate IOLs also are known to possess desriable optical properties (transparency, high refractive index, etc.) and biocompatibility. While pure acrylic IOLs have desirable mechanical, optical and biological properties, they may have unacceptable molecular response times such that the folded or compacted IOL may not unfold as quickly as desired. A pure acrylate IOL fabricated to have a relatively fast molecular response time may be extremely tacky and lack the desired mechanical strength. In this case, the resulting IOL may tear and/or the resulting self-tack can unfolding difficult.

Pure silicone IOLs generally possess excellent mechanical, optical and biological properties similar to pure acrylate IOLs. Unlike acrylic IOLs, silicone IOLs generally possess faster molecular response times. In fact, the silicone IOLs may be so responsive that when folded small enough to be inserted through a 3 mm or smaller incision, the stored energy can cause the IOL to unfold more quickly than desired.

There is a need for a polymeric material with a molecular response time which makes it suitable for use near fragile body tissues, such as within the eye of a subject. There is also a need for ophthalmic devices in which one polymeric material is useful for both low modulus and high modulus elements of a single device to, inter alia, simplify the multi-part polymeric article manufacturing process and create better integrated multi-part polymeric articles in which the various elements of the device have a common value of a property such as a refractive index, but a different value of another property such as modulus, tensile strength, resiliency, or the like.

SUMMARY OF THE INVENTION

The problems associated with previous polymer materials are solved by providing materials that have an average of more than two vinyl terminations. Moduli may be selected by adjusting hydride to vinyl ratio, varying the number of vinyl terminations on the silicone fluid, varying the number of vinyl pendent groups on the silicone fluids, and/or the amount of catalyst. Low modulus polymers prepared as described herein also are ideal starting materials for many products implantable in patients (e.g., IOLs, augmentation implants). In addition, polymers with capable of different degrees of polymerization are described. Polymers with a low degree of polymerization can be useful for pharmaceutical compositions (eg. contact lens solutions), while polymers with a medium degree of polymerization can be useful for topical compositions (eg. hairspray, skin lotions, skin creams) are described. Polymers as described herein can also be used to controllably release a bioactive agent. Embodiments of the present invention may also be utilized in other applications where control of a mechanical property such as material modulus is important.

In one embodiment, a polymer comprising a plurality of monomers has a general structure of formula 1, Formula 1

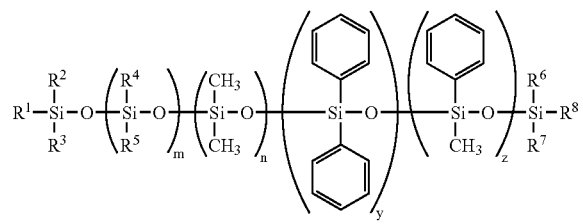

wherein the sum of m and n is x, x ranges from 0 to about 12000, y ranges from 0 to about 500, and z ranges from 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ is $CH=CH_2$, and wherein more than two of $R^1$, $R^2$, $R^3$, $R^6$, $R^7$, or $R^8$ are $CH=CH_2$. In another embodiment, the monomers comprise at least one pendent vinyl group. In another embodiment, the monomers comprise an average of 3 or more vinyl terminations. In another embodiment, the polymer is capable of controlled release of an active agent.

In one embodiment, the polymer has a general structure of formula 2.

Formula 2

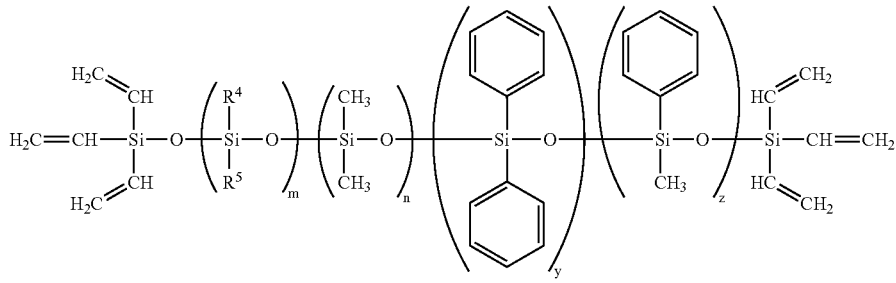

wherein the sum of m and n is x, x ranges from 0 to about 12000, y ranges from 0 to about 500, and z ranges from 0 to about 500, the sum of x, y, and z is at least 1, if m is greater than zero, and at least one of $R^4$ or $R^5$ must be $CH=CH_2$.

In one embodiment, an ocular lens is described which comprises a polymer having a general structure of formula 1, Formula 1

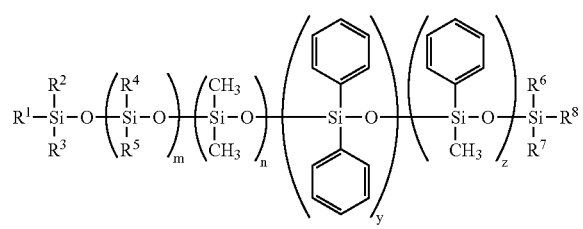

wherein the sum of m and n is x, x ranges from 0 to about 12000, y ranges from 0 to about 500, and z ranges from 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$, and wherein more than two of $R^1$, $R^2$, $R^3$, $R^6$, $R^7$, or $R^8$ are $CH=CH_2$. Herein, the polymer can comprise at least one pendent vinyl group. In one embodiment, the polymer is a hexavinyl terminated silicone fluid.

In one embodiment, the ocular lens is selected from the group consisting of an intraocular lens, a corneal implant, and a contact lens. In another embodiment, the intraocular lens comprises an optic and at least one haptic. In another embodiment, the ocular lens is capable of controlled release of a therapeutic agent.

In one embodiment, the intraocular lens comprises a first portion and a second portion; wherein the first portion and the second portion have a different modulus of elasticity; and wherein the first portion and the second portion have the same or about the same refractive index at a predetermined wavelength in the visible light waveband. In another embodiment, the intraocular lens comprises an optic, wherein the first portion comprises an inner portion of the optic and the second portion comprises an outer portion of the optic dispersed about the inner portion, the portions having same or about the same refractive index at a predetermined wavelength in the visible wavelength band.

In one embodiment, an implantable medical device is described wherein the implantable medical device is made from a polymer comprising a plurality of monomers and has a general structure of formula 1, Formula 1

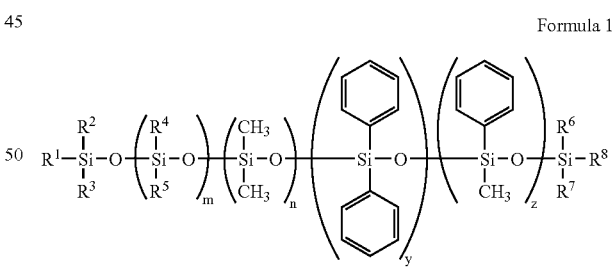

wherein the sum of m and n is x, x ranges from 0 to about 12000, y ranges from 0 to about 500, and z ranges from 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$, and wherein more than two of $R^1$, $R^2$, $R^3$, $R^6$, $R^7$, or $R^8$ are $CH=CH_2$.

In one embodiment, the monomers comprise an average of three or more vinyl terminations. Herein in some embodiments, the monomers can comprise six vinyl terminations. In another embodiment, the implantable medical device is selected from the group consisting of body augmentation implants, breast implants, ocular lenses, and intraocular lenses, further wherein said implantable medical device is capable of controlled release of a therapeutic agent.

In one embodiment, a method of forming an elastomeric article of manufacture comprises (a) providing polymers comprising a plurality of monomers and having the general structure of formula 1,

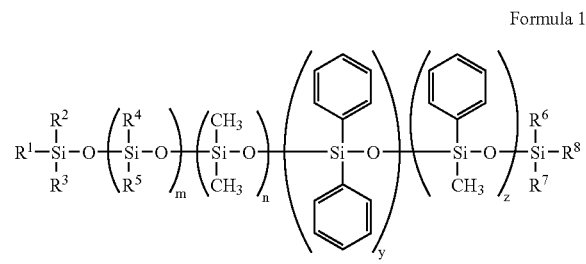

Formula 1 wherein the sum of m and n is x, x ranges from 0 to about 12000, y ranges from 0 to about 500, and z ranges from 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$, and wherein more than two of $R^1$, $R^2$, $R^3$, $R^6$, $R^7$, or $R^8$ are $CH=CH_2$, (b) providing a cross-linker, (c) providing a catalyst, (d) combining said monomers, said cross-linker and said catalyst to form a polymeric mixture and (e) curing said polymeric mixture, wherein at least a portion of said article of manufacture is formed. In another embodiment, the article of manufacture is selected from the group consisting of intraocular lenses, corneal implants, contact lenses, ocular lenses, body augmentation implants, medical device coatings, and breast implants. In another embodiment, the article of manufacture is capable of controlled release of a therapeutic agent.

In one embodiment, a topical composition comprising polymers having the general structure formula:

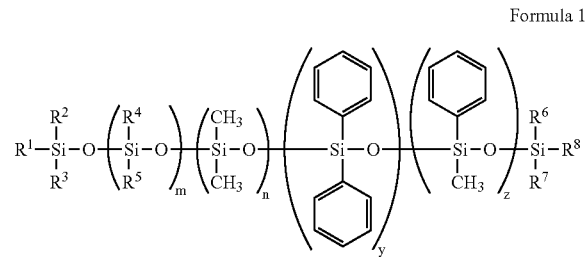

Formula 1 wherein the sum of m and n is x, x ranges from 0 to about 12000, y ranges from 0 to about 500, and z ranges from 0 to about 500, the sum of x, y, and z is at least 1, $R^1$-$R^8$ are each independently $CH_3$, $C_5H_5$ or $CH=CH_2$, if m is greater than zero, at least one of $R^4$ or $R^5$ must be $CH=CH_2$, and wherein more than two of $R^1$, $R^2$, $R^3$, $R^6$, $R^7$, or $R^8$ are $CH=CH_2$. In another embodiment, the topical composition is selected from the group consisting of skin creams, sprays, and lotions. In another embodiment, the topical composition is capable of absorbing UV light. In yet another embodiment, the polymer of the topical composition is capable of controlled release of a therapeutic agent.

Definition of Terms

The terms and phrases used herein shall have the following, non-limiting, definitions.

Elongation: As used herein, "elongation" refers to the act of lengthening or stretching a polymeric material. In some instances, the elongation may be represented by the following formula where L is the length of the elongated polymer and $L_0$ is the length of the corresponding non-elongated polymer: $[L/L_0]$ Full Elongation: As used herein, "full elongation" refers to the act of lengthening or stretching a polymeric material or polymeric IOL to its elastic limit.

Intermediate Elongation: As used herein, "intermediate elongation" refers to the act of lengthening or stretching a polymeric material or polymeric IOL to a point between its original length and limit.

Glass Transition Temperature ($T_g$): As used herein, the "glass transition temperature ($T_g$)" refers to the temperature wherein a polymeric material becomes less elastic and more brittle. For soft polymeric materials, $T_g$ typically is not measured since it may be as low as $-100°$ C. or lower.

Mass percent: As used herein, "mass percent" and "mass %" refer to the mass of monomer present in a polymer divided by the total weight of the polymer multiplied by 100. Mathematically, mass percent is represented by the following formula where $M_m$ is the mass of the monomer and $M_P$ is the mass of the corresponding polymer: $[M_m/M_P] \times 100 =$ Mass Percent.

Compression Modulus or Modulus of Elasticity: As used herein "modulus of elasticity" refers to the ratio of stress to strain. As used herein, "compression modulus" refers to the ratio of compressive stress to compressive strain.

Moduli: As used herein, "moduli" refers to the plural form of modulus or modulus of elasticity.

Percent Elongation: As used herein, "percent elongation" refers to the length of an elongated polymer divided by the length of the original polymer. Mathematically, the percent elongation is represented by the following formula where L is the length of the elongated polymer and $L_0$ is the length of the corresponding non-elongated polymer: $[L/L_0] \times 100 =$ Percent Elongation.

Pliable: As used herein, "pliable" refers to the flexible nature of a polymeric material and to the flexibility of polymeric IOLs that can be folded, rolled or otherwise deformed sufficiently to be inserted through a 2 mm or less surgical incision.

kPa: As used herein, "kPa" refers to kilopascal, which is a unit of pressure or stress and is the equal to 1000×Newton per meter squared ($N/m^2$).

Resiliency: As used herein, "resiliency" refers to a polymeric material's or a polymeric IOL's inherent ability to return to its unstressed configuration following impact, deformation in an inserter, or the resulting deformation associated with the stress on impact, also referred to herein after as "rebound resiliency."

Refractive Index (RI): As used herein, "refractive index (RI)" refers to a measurement of the refraction of light of a material or object, such as an IOL. More specifically, it is a measurement of the ratio of the speed of light in a vacuum or reference medium to the speed of light in the medium of a substance, material, or device under examination. The refractive index of a substance, material, or device typically varies with the wavelength of the light, a phenomenon sometimes referred to as dispersion.

Softness: As used herein, "softness" refers to a polymeric material's or a polymeric IOL's pliability as opposed to, for example, a polymethylmethacrylate (PMMA) IOL that is rigid and hard.

Ultimate Tensile Strength: As used herein, "ultimate tensile strength" refers to the maximum stress a material can withstand before fracture and is measured in psi (lb/in$^2$).

Clear Aperture: As used herein, "clear aperture" refers to the portion of an optic that limits the extent of the rays from an object that contributes to the conjugate image and is generally expressed as a diameter of a circle.

Common Polymeric Material: As used herein, "common polymeric material" refers to similarity of material composition between two objects or portions of an object. Two objects or portions of an object comprise a common polymeric material if the two objects or portions consist essentially of the same base polymer chain or have at least 50% w/w of the same base polymer chain, or 75% w/w of the same base polymer chain, or 85% w/w of the same base polymer chain, or 90% w/w of the same base polymer chain, or 95% w/w of the same base polymer chain, and, when present, the same cross-linking agent.

Common Refractive Index: As used herein, "common refractive index" refers to the similarity of refractive indices between two materials. A common refractive index between two materials would be a difference in refractive index between the two materials of less than or equal to 1% at a predetermined wavelength in the visible light waveband.

DETAILED DESCRIPTION

Embodiments of the present invention may include polymer materials and compositions with moduli that may be altered based, for example, on hydride to vinyl ratio, amount of catalyst, varying the number of vinyl terminations on the silicone fluid, varying the number of pendent vinyl groups on the silicone fluid, and/or MVC content are described herein. Also, low modulus materials are included that exhibit mechanical qualities that make them excellent for implantation in living organisms, particularly animals, more particularly humans. In some embodiment, a low modulus material is used to provide devices including, but not limited to, ophthalmic lenses such as IOLs or contact lenses, breast or other augmentative implants, and controlled release devices (e.g., pharmaceutical formulations). The mechanical qualities and feel of such low modulus materials make it possible to prepare bodily augmentation devices that are implantable in a living organism, for example, breast implants containing little or no liquid. In addition, polymers with different degrees of polymerization are anticipated. In certain embodiments, polymers with a low degree of polymerization are used to provide pharmaceutical compositions (e.g., contact lens solutions). In other embodiments, polymers with a medium degree of polymerization are used to provide topical compositions (e.g., hairspray, skin lotions, skin creams). Polymers as described herein can also be used to controllably release a bioactive agent. Embodiments of the present invention may also be utilized in other applications or devices where control of a mechanical property such as material modulus is important.

As for IOLs, it is desirable they can be folded, rolled or otherwise deformed such that they can be inserted through small incisions. Furthermore, in order to reduce patient trauma and post surgical recovery time, the IOL preferably comprises a responsive polymer that unfolds in a controlled manner. To meet these requirements, the polymers preferably have minimal self tack and do not retain excessive amounts of stored mechanical energy.

Historically, foldable IOL materials have been designed to be tough (tensile strength of greater than 750 pounds per square inch [psi]) and with a relatively high percent elongation (greater than 100%). These properties give the IOL sufficient toughness such that the IOL does not tear from the forces experienced during insertion through a 2.6 to 3.2 mm incision. Presently available foldable IOLs include, among others, Sensar® (Advanced Medical Optics, Santa Ana Calif.), an acrylic IOL having a tensile strength of about 850 psi and an elongation at break of about 140%; SLM-2® (Advanced Medical Optics, Santa Ana Calif.), a silicone IOL having a tensile strength of about 800 psi and an elongation at break of about 230%; and AcrySof® (Alcon Laboratories, Fort Worth, Tex.) having a tensile strength of about 1050 psi. Such IOLs are suitable for insertion through incision sizes of about 2.6 mm or greater.

The polymer materials described herein may be used to form may be used to form ophthalmic devices and other devices that are soft to very soft and may be foldable.

Flexibility in monomer selection is provided herein, which provides for control over the material's mechanical, optical and/or thermal properties. For example, the ability to adjust a material's refractive index (RI) and mechanical properties is important in designing ultra-small incision IOLs. Also, hydrophobic siloxy materials having excellent ocular biocompatibility are anticipated. Thus, it surprisingly has been discovered that by utilizing the silicone materials according to embodiments of the present invention an IOL optic can be made that has properties permitting passage of the IOL through an ultra small incision without damage to the IOL, the inserter cartridge, or the eye. In addition, the IOL may have at least one resilient haptic that shares a common siloxy monomer with the optic.

In certain embodiment, silicone materials having unique properties are derived from the inherent flexibility of the siloxane bond. The alternating silicon-oxygen polymer backbone of siloxanes may make them remarkably more flexible than their organic counterparts that have a carbon-oxygen backbone. This property of siloxanes results in low glass-transition temperatures ($T_g$) and excellent flexibility. Furthermore, a low initial modulus is another important attribute of the novel siloxanes. In order to pass through the insertion cartridge, a refractive IOL is desirably capable of elongating up to about 100%. Therefore, it may be important that the initial modulus is at desirable levels. A low initial modulus translates to low stimulus required to express the IOL through the cartridge. Further, when a desired amount of selected siloxanes, cross linkers and catalysts are combined, the resulting material may have the flexibility and modulus required to make, for example, the optic portion of an IOL suitable for insertion through a small incision without harming the IOL, the inserter cartridge, or the eye.

In some embodiments, an intraocular lens comprises an optic and a haptic made from a common polymeric material so that they also have a common refractive index; however, the optic and haptic have mechanical property that is different for each. In some embodiments, the IOL may be formed according to an embodiment so that the optic and haptic have different moduli of elasticity. For example, an accommodating IOL may be formed so that the optic has a lower modulus than the haptic, thus allowing the relatively stiff haptic to protrude inside the relatively soft optic without causing unwanted reflections due to a refractive index mismatch at interfaces between the optic and the protruding haptic.

Examples of accommodating IOLs having a stiffer protruding haptic are disclosed in co-pending U.S. patent application Ser. Nos. 11/618,411, 11/618,325, and 11/864,450, which are herein incorporated by reference in their entirety One way to adjust moduli between the haptic and optic may be provided by an adjustment in the amount of cross-linker and/or catalyst and/or MVC content of each IOL component. Embodiments herein may be used to provide IOL's in which at least the optic thereof has a modulus that is less than about 100 kPa, less than 75 kPa, or even less than 50 kPa or 25 kPa. The stiffness of the haptic may be greater than 500 kPa, or greater than 3000 kPa, depending on the particular design requirements. In some embodiments, the modulus of the haptic is greater than that of the optic by at least 50%, by at least 150%, by at least 250%, or by at least 500%. In some embodiments, the modulus may vary continuously over at least some interface regions between the haptic and the optic, for example, to provide a particular performance or stress distribution over the IOL in reaction to an external force on the IOL (e.g., an ocular force produced by the capsular bag, zonules, or ciliary muscle of an eye into which the IOL is inserted).

In some embodiments, an ophthalmic lens, such as an intraocular lens, comprises an optic having a clear aperture that comprises an inner portion and an outer portion disposed about said inner portion. The inner portion and outer portion comprise a common polymeric material and may have a common refraction index; however, the inner portion has a modulus that is different from that of the outer portion. The difference in modulus may be selected, for example, to control the amount and/or form of deformation of the optic in reaction to an external force such as an ocular force produced by the capsular bag, the zonules, and/or the ciliary muscle of an eye into which the optic is placed. In some embodiments, the refractive index may also vary between the zones, for example, to control aberrations of the optic in a stressed or unstressed state.

The modulus of the inner portion of the optic may by greater than or less than that of the outer portion, depending of the particular design requirements. In some embodiments, the optic comprises three or more zones disposed within the clear aperture of the optic. In other embodiments, the modulus of at least portions of the optic may vary continually, for example, by producing a catalyst gradient throughout a polymeric fluid used to form the optic. In some embodiments, the zones of the optic may have an ellipsoid or similar shape, such that the modulus varies from the center of the optic outward in a three-dimensional manner. Alternatively or additionally, the variation in modulus of the zones may vary in a two dimensional manner, for example, forming concentric rings as the modulus varies in radial direction from the optical axis of the optic. The difference in modulus between two zones of the optic may be greater than or equal to 5%, or greater than or equal to 15%, or greater than or equal to 25%, or greater than or equal to 50%, depending on the number of zones and the desired performance of the optic under a given loading force.

Some embodiments may provide a relatively low modulus material that is particularly suitable for use in at least the optic of an accommodating IOL. For example, an adjustment in the amount of cross-linker, number of vinyl terminations, number of vinyl pendent groups, catalyst and/or MVC content, the haptic portion of an IOL or accommodating IOL may be made. Embodiments may be used to provide IOL's in which at least the optic thereof has a modulus that is less than about 100 kPa, less than 75 kPa, or even less than 50 kPa or 25 kPa.

The materials made may have low initial moduli and a low glass transition temperature ($T_g$). Moreover, the IOLs may be multifocal (either refractive or diffractive), accommodating (e.g., deformable or movable under the normal muscle movements of the human eye), highly biocompatible and have RIs ranging from about 1.40 to about 1.56, preferably from about 1.41 to about 1.52, for light in the visible wavelengths. These and other objects described herein may be achieved by providing an unsaturated terminated silicone fluid and cross-linking it using a hydride cross-linking agent and platinum catalyst. The unsaturated terminated silicone fluid, in some embodiments, can have more than three vinyl terminations. In different embodiments, the unsaturated terminated silicone fluid can have three, four, five or six vinyl terminations. In another embodiment, metals aside from platinum, more preferably transition metals, may be used. Herein, silicone fluids are disclosed that may be cross-linked to prepare polymers with different moduli.

The unsaturated terminated siloxanes are preferably vinyl terminated siloxanes, more preferably multi-vinyl terminated. Non-limiting examples include vinyl terminated diphenylsiloxane-dimethylsiloxane copolymers, vinyl terminated polyphenylmethylsiloxanes, vinyl terminated phenylmethylsiloxane-diphenyldimethylsiloxane copolymers, vinyl terminated polydimethylsiloxanes and methacrylate, and acrylate functional siloxanes. Other suitable silicone materials are disclosed in U.S. Pat. No. 6,361,561, the entirety of which is incorporated herein by reference. Representative materials can be obtained from Gelest, Inc. (Morrisville, Pa.) or synthesized using methods known to those skilled in the art.

In one embodiment, the unsaturated terminated siloxane is a vinyl terminated siloxane comprising polymers of the structure depicted in Formula 1 below (herein referred to as "silicone fluid"). In other embodiments, polymers can consist of greater than 50% w/w having the structure of Formula 1, or greater than 75% w/w having the structure of Formula 1, or greater than 85% w/w having the structure of Formula 1, or greater than 90% w/w having the structure of Formula 1, or greater than 95% w/w having the structure of Formula 1. The values for x, y, and z will vary depending on, for example, the desired RI of the lens; and, in Formula 1, x is equal to the sum of m and n and is preferably at least about 1. In one embodiment, the sum of x, y, and z is greater than or equal to about 1. Preferably, IOLs produced have an RI of at least 1.40, more preferably at least 1.43. For example, if an IOL having a refractive index ("RI") of 1.43 is desired, the x:y:z ratio may be approximately 30:1:1; a x:y:z ratio of about 12:1:2 will result in an IOL having a RI of approximately 1.46. Skilled artisans can prepare an IOL having a desired RI, optical clarity and mechanical properties by adjusting the x:y:z ratio using skills known in the art and without undue experimentation. In one embodiment, x ranges from 0 to about 12000, y ranges from 0 to about 500, z ranges from 0 to about 500, and the sum of x, y, and z is greater than or equal to 1. In another embodiment, x ranges from about 10 to about 12000, y ranges from about 1 to about 500, z ranges from 0 to about 500, and the sum of x, y, and z is from about 100 to about 15000. In another embodiment, x+y+z has a minimum value of about 200 in order to provide a high softness polymer (e.g., when required for optic portions of an IOL). $R^1$-$R^8$ are each independently $CH_3$, $C_6H_5$ or $CH=CH_2$. If m is greater than zero, at least one of $R^4$ or $R^5$ must be $CH=CH_2$. In one embodiment, more than two of $R^1$, $R^2$, $R^3$, $R^6$, $R^7$, and $R^8$ are $CH=CH_2$.

Formula 1

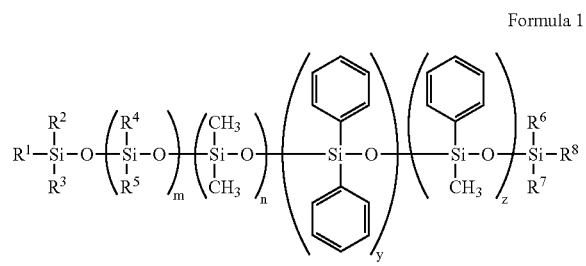

In another embodiment, at least four of $R^1$, $R^2$, $R^3$, $R^6$, $R^7$, and $R^8$ are $CH=CH_2$. In another embodiment, at least five are $CH=CH_2$. In yet another embodiment, all six of $R^1$, $R^2$ $5$ $R^3$, $R^6$, $R^7$, and $R^8$ are $CH=CH_2$. The utility of more vinyl terminations, as well as vinyl pendent groups, is to provide the polymer with additional ability to crosslink, the ability to bind molecules it would otherwise not be able to bind and provide additional sites of chelation.

In one embodiment, the silicone fluid can be hexavinyl terminated, wherein $R^1$, $R^2$, $R^3$, $R^6$, $R^7$, and $R^8$ can be vinyl terminated and can be represented by formula 2. In other embodiments, polymers can consist of greater than 50% w/w having the structure of Formula 2, or greater than 75% w/w having the structure of Formula 2, or greater than 85% w/w having the structure of Formula 2, or greater than 90% w/w having the structure of Formula 2, or greater than 95% w/w having the structure of Formula 2. The values for x, y, and z will vary depending on, for example, the desired RI of the lens; and, in Formula 3, x is equal to the sum of m and n. In one embodiment, the sum of x, y, and z is greater than or equal to about 1. Preferably, IOLs produced have an RI of at least 1.40, more preferably at least 1.43. For example, if an IOL having a refractive index ("RI") of 1.43 is desired, the x:y:z ratio may be approximately 30:1:1; a x:y:z ratio of about 12:1:2 will result in an IOL having a RI of approximately 1.46. Skilled artisans can prepare an IOL having a desired RI, optical clarity and mechanical properties by adjusting the x:y:z ratio using skills known in the art and without undue experimentation. In one embodiment, x ranges from 0 to about 12000, y ranges from 0 to about 500, z ranges from 0 to about 500, and the sum of x, y, and z is greater than or equal to 1. In another embodiment, x ranges from about 10 to about 1200, y ranges from about 1 to about 500, z ranges from 0 to about 500, and the sum of x, y, and z is from about 100 to about 2200. In another embodiment, x+y+z has a minimum value of about 200 in order to provide a high softness polymer (e.g., when required for optic portions of an IOL). If m is greater than zero, at least one of $R^4$ or $R^5$ must be $CH=CH_2$.

Combinations for the sum of x+y+z exist for sums from at least 1 to about 15000. In addition, the sum can determine what type of material is formed. In one embodiment, for example, the sum can be less than about 100, in which case, the material can be a liquid and can be used as a liquid carrier formulation, for example, eye drops or hair spray. In another embodiment, the sum can be from about 100 to about 1000, wherein the material can be a more viscous liquid or gel. In one embodiment, the material can be used in topical compositions, for example, skin creams and lotions. In one embodiment, the skin cream can absorb harmful light. In another embodiment, the sum can be from about 300 to about 1200, wherein the material can be formed as an elastomeric. In such an embodiment, the materials formed as elastomerics can be used to form such items as lenses. Each of the embodiments described above can be used with other appropriate additives with or without further cross-linking reactions.

Optionally, a number of ultraviolet (UV) and blue light absorbing dyes can be added to the silicone polymers. For example, the silicone IOLs may include 0.1 to 1.5 mass % of UV and blue light absorbing compounds such as benzophenone and benzotriazole-based UV light absorbers or blue light blocking dyes including azo and methine yellow, which selectively absorb UV/blue light radiation up to about 450λ. See, for example, U.S. Pat. Nos. 5,374,663; 5,528,322; 5,543,504; 5,662,707; 6,277,940; 6,310,215 and 6,326,448, the entire contents of which are incorporated herein by reference.

A variety of initiators for polymerization reactions can be employed. In one non-limiting embodiment, peroxide initiators are used. Examples of peroxide initiators include, without limitation, about 0.100 to about 1.50 mass % of di-tert-butyl peroxide (Trigonox® a registered trademark of Akzo Chemie Nederland B.V. Corporation Amersfoort, Netherlands) or 2,5-dimethyl-2,5-bis(2-ethylhexanoylperoxy) hexane. It should be noted that peroxide initiators initiate the cross-linking of vinyl groups on monomers (e.g., those on divinyl-terminated silicone monomers). While this can help facilitate the cross-linking of the silicone monomers, at least some of the hydride groups must still be cross-linked.

One or more monomers may be cross-linked utilizing one or more hydride-containing cross-linkers such as, but not limited to: nonpolymetric X-linkers such as phenyltris(dimethylsiloxy)silane (Formula 3 below), tetrakis(dimethylsiloxy)silane (Formula 4 below), 1,1,3,3-tetraisopropyldisiloxane, 1,1,3,3-tetramethyldisiloxane, 1,1,4,4-tetramethyldisilethane bis(dimethylsilyl)ethane, 1,1,3,3-tetramethyldisilazane; hydride terminated polymeric X-linkers with different molecular weights such as hydride terminated polydimethylsiloxane (DMS-H03, DMS-H11 to DMS-H41), hydride terminated polyphenyl-(di-methylhydrosiloxy)siloxane (HDP-111, Formula 5 below, wherein W Formula 2

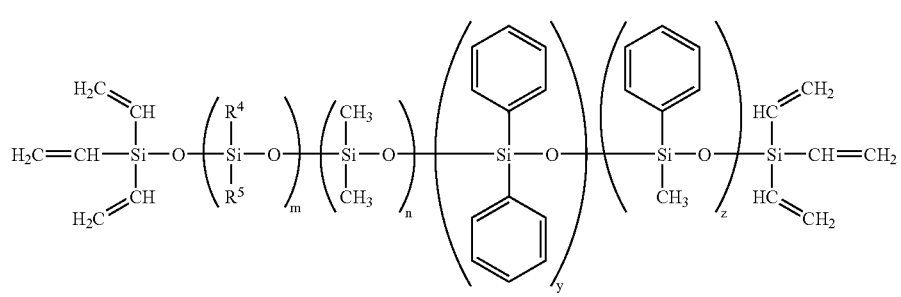

is about 5 to about 50); hydride terminated methylhydrosiloxane-phenylmethylsiloxane copolymer (HPM-502), which are commercially available from Gelest; nonhydride terminated polymeric cross-linkers such as methylhydrogen dimethylsiloxane (XL-103, XL-110, XL-111, XL-112, XL-115), which are commercially available from Nusil; and trimethylsiloxane terminated methylhydrosiloxane-dimethylsiloxane copolymer (HMS-013, HMS-031, HMS-082, HMS-301), trimethylsilyl terminated polymethylhydrosiloxane (HMS-991), which are commercially available from Gelest. Other cross-linkers such as hydride Q resins may also be used to improve the mechanical properties of the gels. The softness of the final gel formulations depends on the relative amount of cross-linker to vinyl silicone fluid (e.g., H/V [hydride-vinyl] ratio).

Formula 3

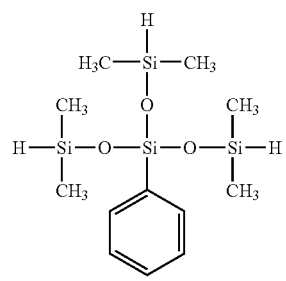

Phenyltris(dimethylsiloxy)silane

Formula 4

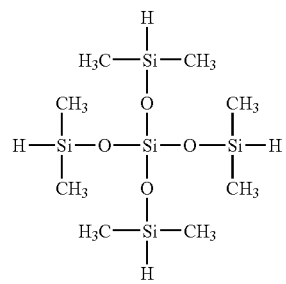

Tetrakis(dimethylsiloxy)silane

Formula 5

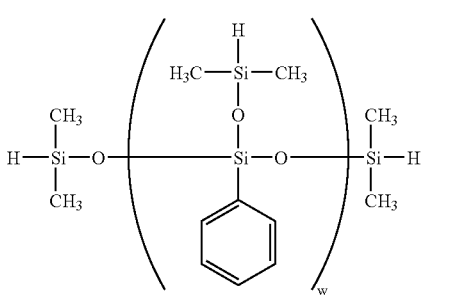

Hydride-terminated Polyphenyl-(di-methylhydrosiloxy)siloxane

Properties of the silicone materials such as modulus, percent weight loss may be changed by varying the ratio of hydride and vinyl contents (H/V ratio) in the silicone fluids. Vinyl content of a silicone fluid may be determined by, for example, the GPC method, titration, or NMR (nuclear magnetic resonance spectroscopy). By varying the ratio of hydride primarily from the cross-linker and vinyl primarily from the vinyl silicone fluid, silicone materials with different moduli may be obtained. In certain embodiments, the H/V ratio may be at least about 0.1, more preferably at least about 0.5, more preferably about 0.6, more preferably about 0.7, more preferably about 0.8, more preferably about 0.9, more preferably about 1.0, more preferably about 1.1, more preferably about 1.25, and more preferably at most about 1.5.

In certain embodiments, the modulus of material may be affected by the amount of catalyst and/or methyl-vinyl cyclics ("MVCs"). In certain embodiments, as the amount of catalyst and/or MVCs is increased, the modulus of the material may also increase until a peak modulus is reached. In certain embodiments, after a peak modulus is reached, the modulus may begin to level off or, in some cases, may decrease.

In certain embodiments, the MVC may be any methylvinyl siloxane, which includes cyclosiloxane and non-cyclosiloxane classes of materials. Nonlimiting examples of methylvinyl cyclosiloxane classes include tetramethylvinylcyclotetrasiloxane and pentamethylvinylcyclopentasiloxane. Non-cyclosiloxane classes include 1,3-tetramethyldisiloxane, divinyltetraphenyidisiloxane, 1,5-divinylhexamethyltrisiloxane, and 1,5-divinyl-3,3-diphenyltetramethyltrisiloxane. One example of an MVC is 1,3,5,7-tetravinyl-1,3,5,7-tetramethylcyclotetrasiloxane. In certain embodiments, the MVC may be present in an amount of at least about 0.01% or at most about 1% by weight. It should be understood that for certain polymer embodiments described herein, MVCs may partially substitute the catalyst, augment the catalyst or be used to alter the H/V ratio. The MVC, in certain embodiments, may have an inversely proportional impact on the moduli of polymers prepared therewith.

In general, platinum-containing catalysts work well. Exemplary platinum catalyst include platinum-tetravinyltetramethylcyclotetrasiloxane complex, platinum carbonyl cyclovinylmethylsiloxane complex, platinum cyclovinylmethylsiloxane complex, platinum octanaldehyde/octanol complex. Many different platinum catalysts may be used depending on, inter alia, the desired pot life. Preferably, the platinum catalyst is used in amounts by weight of at least about 0.01%, more preferably at least about 0.05%, even more preferably at least about 0.1%. Preferably, the platinum catalyst is used in amounts of about 1% or less, more preferably about 0.75% or less, even more preferably about 0.5% or less, even more preferably about 0.4%, even more preferably about 0.3%, even more preferably about 0.2%.

In addition to platinum catalysts, other metal catalysts can be used. In some embodiments, transition metals can be used as catalysts, more specifically, palladium and rhodium catalysts can be used. Complexes and salts of metal catalysts can be used. An example of a transition metal complex used as a catalyst is tris(dibutylsulfide) rhodium trichloride.

For certain embodiments and without wishing to be bound by theory, one reason for the impact of some catalysts, especially platinum catalysts, on the modulus may be due to the presence of an inhibitor or stabilizer that may reduce the hydride/vinyl ratio and/or may prevent complete curing. An example of such an agent may be an MVC such as cyclovinylmethylsiloxane (e.g., 1,3,5,7-tetravinyl-1,3,5,7-tetramethylcyclotetrasiloxane). It is worthwhile to note that in certain embodiments, the effects of catalyst amounts on modulus may be independent of curing time. While MVCs may sometimes be used as stabilizers in catalysts to, for example, keep platinum suspended in solution, the MVCs may be present in such small amounts that they may be inert.

In certain embodiments, the platinum catalyst level for a polymer may be increased to levels significantly higher than conventionally used (e.g., up to 50 ppm versus a more traditional 10 ppm or less). A skilled artisan may expect that as catalyst concentration increases, curing time may decrease and polymer cross-linking may increase. The skilled artisan may also expect this to lead to a more rigid or firm polymer (even assuming curing temperature may be the same). In certain embodiments, the catalyst may be increased to atypical levels and a significant decrease in curing time may be observed.

In certain embodiments, the resulting polymer may be far less rigid and less firm than expected. In certain embodiments, excessive amounts of catalyst may be used and the corresponding increase in MVCs may allow them to become reactive ingredients and may end-cap the hydrides on the cross-linkers, which may result in more free ends on the structural polymers. The additional free ends may provide a less-cross-linked and, therefore, less rigid polymer. As a skilled artisan will appreciate, in certain embodiments, such a polymer may be ideal for preparing many products including, but not limited to, products implantable in patients (e.g., IOLs, augmentation implants).

In certain embodiments, the MVC may be present in an amount of at least about 0.01%, about 0.05%, about 0.1%, about 0.11%, about 0.15%, about 0.2%, or about 0.25% by weight; to at most about 1%, about 0.75%, about 0.5%, about 0.4%, about 0.39%, about 0.35%, or about 0.35% by weight. In certain embodiments, the MVCs may partially substitute the catalyst in any proportion or amount including completely or the MVC may augment the catalyst. In certain embodiments, the MVC may have an inversely proportional impact on the moduli of polymers prepared therewith. Certain embodiments described herein may incorporate the teachings regarding MVCs and their relationship to the moduli of polymer articles prepared therefrom.

When used for IOL optic portions, a polymer with a low initial modulus prepared as described herein facilitates a more easily inserted IOL by reducing the force required to express the polymer IOL through an inserter cartridge. In addition, the same starting materials may be used for both optic and haptic portions (only varying the H/V ratio and/or % catalyst or, MVC); therefore, the material supply and manufacture of IOLs is simplified. An added benefit of using the same starting materials is that the resulting optic and haptic portions will be more compatible thereby facilitating more robust and/or seamless fusion.

In another embodiment, the polymers described herein can be used in a composition for topical administration. An example of a topical composition can be a skin cream, lotion, skin spray, or skin powder. The polymers can have double bonded vinyl terminations, wherein the double bonds can be broken by wavelengths of light. An exemplary, non-limiting, example of wavelengths of light absorbable by the polymers described herein are wavelengths of light in the UV region. One skilled in the art will appreciate that UV light can be absorbed by the double bonds. The absorption of UV light can generate radicals, for example, but not limited to, radicals in the form of electrons. The radicals can combine or be reabsorbed by the polymer, or surrounding polymers in the composition. The combination and reabsorbing of radicals by the polymer can result in an overall stable composition.

In one embodiment, the polymer may be used as a controlled release polymer for formulating therapeutic agents. In addition, the polymer may be used to prepare dual use implantable or wearable medical devices (e.g., IOLs and contact lenses) whereby the device serves a particular purpose as well as controllably releasing therapeutic agents. For example, the polymer may be used to prepare an IOL that controllably releases a therapeutic agent for "dry eye." A skilled artisan can envision several devices, conditions, and/or therapeutic agents in conjunction with this embodiment.

Example 1

Preparation of Polymers

A. The following is an example of the synthesis of a hexavinyl terminated silicone fluid without pendent vinyl groups. In a method for making this polymer (polymer B38), 103.48 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 691.78 grams of octamethylcyclotetrasiloxane and 5.15 grams of hexavinyl dislioxane were added together to the reaction kettle. Then, 3.17 grams of tetramethylammonium siloxanolate was added to the reaction kettle. Stirring continued for at least 68 hours at 105° C. (±10° C.). The temperature of the kettle was then raised to 150° C. (±20° C.) for at least 5 hours. After cooling, the silicone fluid was filtered through a 0.2 micron filter.

B. The following is an example of the synthesis of a hexavinyl terminated silicone fluid with pendent vinyl groups. In a method for making this polymer (polymer B37), 129.35 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 666.32 grams of octamethylcyclotetrasiloxane, 59.72 grams of tetravinyltetramethylcyclotetrasiloxane and 5.53 grams of hexavinyl dislioxane were added together to the reaction kettle. Then, 4.54 grams of tetramethylammonium siloxanolate was added to the reaction kettle. Stirring continued for at least 25 hours at 105° C. (±10° C.0). The temperature of the kettle was then raised to 150° C. (±20° C.) for at least 5 hours. After cooling, the silicone fluid was filtered through a 0.2 micron filter.

C. The following is an example of the synthesis of a high refractive index hexavinyl terminated silicone fluid. In a method for making this polymer (polymer B29), 249.63 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 546.57 grams of octamethylcyclotetrasiloxane and 5.07 grams of hexavinyl dislioxane were added together to the reaction kettle. Then, 3.36 grams of tetramethylammonium siloxanolate was added to the reaction kettle. Stirring continued for at least 72 hours at 105° C. (±10° C.). The temperature of the kettle was then raised to 150° C. (±20° C.) for at least 5 hours. After cooling, the silicone fluid was filtered through a 0.2 micron filter.

D. The following is an example of the synthesis of a high refractive index, high viscosity hexavinyl terminated silicone fluid. In a method for making this polymer (polymer B49), 266.48 grams of octaphenylcyclotetrasiloxane was placed in a preheated 1000 mL reaction kettle at 105° C. (±10° C.). The mechanical stirrer was turned on and the system was purged with nitrogen for at least 30 minutes. Next, 530.65 grams of octamethylcyclotetrasiloxane and 2.56 grams of hexavinyl dislioxane were added together to the reaction kettle. Then, 3.89 grams of tetramethylammonium siloxanolate was added to the reaction kettle. Stirring continued for at least 18 hours at 105° C. (±11° C.). The temperature of the kettle was then raised to 150° C. (±20° C.) for at least 5 hours. After cooling, the silicone fluid was filtered through a 0.2 micron filter.

A Pope 2" Wiped-Film stills unit was used to remove the volatile components of the above silicone fluids (B38, B37, B29, and B49) by setting the chiller temperature to 5° C., still body temperature to 160° C., the vacuum range to 0.3-2.0 torr and the rotor speed in the range of about 50 to about 70 RPM. A total of about 10% to about 25% of the volatile components were removed from the silicone fluids.

Next, 0.125 grams of 2-(3'-t-butyl-2'-hydroxy-5'-vinyl-phenyl)-5-chlorobenzotriazole (UVAM) was added to 50 grams of the above silicone fluids. After centrifugal mixing, the fluids were placed in the 60° C. oven for 2 to 3 days until the UVAM was completely dissolved in the silicone fluids to make "0.25% UVAM silicone fluids."

Example 2

Preparation of Disc 1

In a vessel, 0.045 grams of platinum-cyclovinylmethylsiloxane complex, was added to 15 grams of the B38 0.25% UVAM silicone fluid. The mixture was well mixed by high speed centrifugation at least twice for 30 seconds. The resulting formed "Part A" of the silicone fluid. The final catalyst concentration of three otherwise identical silicone fluids was, by weight, about 0.1%, to about 0.5%. In a separate vessel, "Part B" of the silicone fluid was prepared by mixing 0.4038 grams of 25-30% methylhydrosiloxane-dimethylsiloxane copolymer, trimethylsiloxane termineated, (HMS-301 from Gelest) with 5 grams of the B38, 0.25% UVAM silicone fluid prepared above. Five grams of Part A and 5 grams of Part B were mixed in a vessel with a theoretical H/V ratio=1.0.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 40 kPa and after one day static extraction with IPA, the modulus was 49 kPa. Refractive indices, measured at 19.5° C. (±1° C.), of the disks before and after extraction were 1.434 and 1.433 respectively.

Example 3

Preparation of Disc 2

In another example, In a vessel, 0.045 grams of platinum-cyclovinylmethylsiloxane complex, was added to 15 grams of the B38 0.25% UVAM silicone fluid. The mixture was well mixed by high speed centrifugation at least twice for 30 seconds. In a separate vessel, "Part B" of the silicone fluid was prepared by mixing 0.0908 grams of phenyltris(dimethylsiloxy)silane and 5 grams of B38 silicone fluid. Five grams of Part A and 5 grams of Part B were mixed in a vessel with a theoretical H/V ratio=0.5.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 18 kPa and after one day static extraction with IPA, the modulus was 20 kPa. Refractive indices of the discs before and after extraction were 1.435 and 1.433 respectively.

Example 4

Preparation of Disc 3

A silicone fluid with a high refractive index was prepared according to the following. Part A was prepared by adding 0.045 grams of platinum cyclovinylmethylsiloxane complex to 15 grams of B29 silicone fluid with 0.25% UVAM. Part B was prepared by adding 1.0919 grams of hydride terminated polydimethylsiloxane (DMS-H03 from Gelest) to 15 grams of B29 silicone fluid. Five grams of both Part A and Part B were added to a vessel and mixed with a theoretical H/V ratio=1.0.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 47 kPa and after one day static extraction with IPA, the modulus was 54 kPa. Two disks of each were also placed in a soxhlet extraction unit and extracted with IPA for an extended period of time. After extracting for 1, 3, and 5 days, moduli of these samples were 56, 54 and 51 kPa respectively. Refractive index of the discs before extraction was 1.466. Refractive index was 1.465 after one and three days of soxhlet extraction and 1.464 after 5 days of soxhlet extraction.

Example 5

Preparation of Disc 4

A silicone fluid was prepared according to the following. Part A was prepared with 0.25% UVAM B49 silicone fluid and 0.1% platinum cyclovinylmethylsiloxane complex. Part B was prepared by adding 0.4294 grams of hydride terminated polydimethylsiloxane (DMS-H03 from Gelest) to 10 grams of B49 silicone fluid. Five grams of both Part A and Part B were added to a vessel and mixed with a theoretical H/V ratio=1.2.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 36 kPa and after one day static extraction with IPA, the modulus was 44 kPa. Pot life of the fluid was 6 hours. Refractive indices of the discs before and after static extraction were 1.471 and 1.470 respectively.

Example 6

Preparation of Disc 5

A silicone fluid was prepared with high refractive index and high viscosity silicone fluid. Part A was prepared with 0.25% UVAM B49 silicone fluid and 0.1% platinum carbonyl cyclovinylmethylsiloxane complex. Part B was prepared by adding 0.4294 grams of hydride terminated polydimethylsiloxane (DMS-H03 from Gelest) to 10 grams of B49 silicone fluid. Five grams of both Part A and Part B were added to a vessel and mixed with a theoretical H/V ratio=1.2.

The resulting silicone mixture was poured into a Teflon® mold and the mold was placed in an oven at 140° C. for 10 minutes. Moduli of these discs (before and after extraction) were measured using a Q800 DMA (TA Instruments). Diameter and thickness of the sample was measured using a calibrator. After loading the sample on the holder, the temperature of the system was raised to 35° C. and held at equilibrium for 5 minutes before testing. Ramp force was applied to the disk at 1 N/min to the maximum of 9 N/min. The modulus was determined by the slope of two elongation points (4% and 8%) from the curve. Modulus before extraction was 24 kPa and after one day static extraction with IPA, the modulus was 43 kPa. Pot life of the fluid was 20+ hours. The extended pot life would provide flexibility in the manufacturing process.

Example 7

Preparation of Silicone Fluid with Greater than Three but Less than Four Vinyl Terminations This example describes the synthesis of a silicone fluid with an average of 3.74 vinyl terminations. The silicone fluid is prepared by placing 332.03 grams of octaphenylcyclotertasiloxane in a preheated 1000 mL reaction kettle at 105° C. (±10° C.) and stirring. Then, the system is purged with nitrogen for 30 min. After the system is purged, into the reaction kettle is charged 659.60 grams of octamethylcyclotetrsiloxane, 1.75 grams of hexavinyl disiloxane, and 1.80 grams of 1,3-divinyltetramethyl disiloxane. Then, 2.73 grams of tetramethylammonium siloxanolate were added to the reaction mixture. The mixture was kept stirring for at least 20 hours at 105° C. (±10° C.). Then, the temperature of the kettle was raised to 150° C. (±20° C.) for at least five hours. The product of the reaction was then allowed to cool to room temperature. After cooling, the silicone fluid was filtered through a 0.5μ filter and then wiped dry. The resulting silicone fluid had an average of 3.74 vinyl terminations and may have a refractive index of about 1.47.

Example 8

Preparation of Silicone Fluid with Four Vinyl Terminations

A silicone fluid with the average of 4 vinyl terminated groups may be prepared by charging 332.06 grams of octaphenylcyclotetrasiloxane, 659.65 grams of octamethylcyclotetrasiloxane, 2.08 grams of hexavinyl disiloxane, and 1.65 grams of 1,3 divinyltetramethyl disiloxane into a reaction kettle. Then 2.50 grams of tetramethylammonium siloxanolate may be added to the kettle and the reaction mixture may be kept stirring for at least 20 hours at 105° C. (±10° C.). Then, the temperature of kettle may be raised to 150° C. (±20° C.) for at least 5 hours. After cooling, the silicone fluid may be filtered through 0.5μ filter before wiped-film process. The resulting silicone fluid may have a refractive index of about 1.47.

Example 9

Preparation of Silicone Fluid with High Refractive Index

A high refractive index (RI=1.523), high viscosity, hexavinyl terminated silicone fluid was prepared as follows. To a 1000 mL preheated reaction kettle was charged 457.03 grams of octaphenylcyclotetrasiloxane at 105° C. (±10° C.). After turning on the mechanical stirrer, the whole system was purged with nitrogen for at least 30 minutes. Then, 340.84 grams of octamethylcyclotetra-siloxane and 2.15 grams of hexavinyl disiloxane were added to the kettle. Then, 7.35 grams of tetramethylammonium siloxanolate were added initially to the kettle and the reaction mixture was kept stirring for at least 3 hours at 105° C. (±10° C.). Then, an additional 2.04 grams of tetramethylammonium siloxanolate were added to the mixture and the mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The viscosity of this fluid was around 78,000 cp and the refractive index was 1.523.

Example 10

Preparation of Silicone Fluid with a Low Degree of Polymerization

A hexavinyl terminated silicone fluid was prepared as follows. To a 1000 mL preheated reaction kettle was charged 259.77 grams of octaphenylcyclotetrasiloxane at 105° C. (±10° C.). After turning on the mechanical stirrer, the whole system was purged with nitrogen for at least 30 minutes. Then, 199.23 grams of octamethylcyclotetra-siloxane and 46.4 grams of hexavinyl disiloxane were added to the kettle. Then, 3.06 grams of tetramethylammonium siloxanolate were added initially to the kettle and the reaction mixture was kept stirring for at least 3 hours at 105° C. (±10° C.). Then, an additional 2.47 grams of tetramethylammonium siloxanolate were added to the mixture, then another 1.50 grams, and then the mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The refractive index was 1.52. The sum of x+y+z (equal to the degree of polymerization) was about 22. This silicon fluid can be useful in formulating, for example, but not limited to, contact lens solutions and hair sprays.

Example 11

Preparation of Silicone Fluid with a Low Degree of Polymerization

A hexavinyl terminated silicone fluid was prepared as follows. To a 1000 mL preheated reaction kettle was charged 250.26 grams of octaphenylcyclotetrasiloxane at 105° C. (±10° C.). After turning on the mechanical stirrer, the whole system was purged with nitrogen for at least 30 minutes. Then, 181.87 grams of octamethylcyclotetra-siloxane and 18.08 grams of hexavinyl disiloxane were added to the kettle. Then, 2.70 grams of tetramethylammonium siloxanolate were added to the kettle and the reaction mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The refractive index was 1.53. The sum of x+y+z (equal to the degree of polymerization) was equal to about 50. This silicon fluid can be useful in formulating, for example, but not limited to, contact lens solutions and hair sprays.

Example 12

Preparation of Silicone Fluid with a Medium Degree of Polymerization

A hexavinyl terminated silicone fluid was prepared as follows. To a 1000 mL preheated reaction kettle was charged 109.05 grams of octaphenylcyclotetrasiloxane at 105° C. (±10° C.). After turning on the mechanical stirrer, the whole system was purged with nitrogen for at least 30 minutes. Then, 236.05 grams of octamethylcyclotetra-siloxane and 3.56 grams of hexavinyl disiloxane were added to the kettle. Then, 2.00 grams of tetramethylammonium siloxanolate were added to the kettle and the reaction mixture was kept stirring for at least 40 hours at 105° C. (±10° C.). The temperature of kettle was raised to 150° C. (±20° C.) for at least 5 hours. After cooling, the silicone fluid was filtered through 0.5μ filter before wiped-film process. The refractive index was 1.46. The sum of x+y+z (equal to the degree of polymerization) was equal to about 248. This silicon fluid can be useful in formulating, for example, but not limited to, topical skin compositions such as skin creams and lotions.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used herein (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate and do not pose a limitation on the scope otherwise claimed. No language in the specification should be construed as indicating that any non-claimed element is essential to the embodiments disclosed herein.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode, if known to the inventors at the time of filing. Of course, variations on these described embodiments will become apparent to those of ordinary skill in the art upon, reading the foregoing description. The inventor expects skilled artisans to employ such variations as appropriate. Practice of modifications and equivalents of the subject matter recited in the claims is expected. Moreover, any combination of the above-described elements in all possible variations thereof is encompassed herein unless otherwise indicated or otherwise clearly contradicted by context.

Furthermore, references have been made to patents and printed publications throughout this specification. Each of the above-cited references and printed publications individually are incorporated herein by reference in their entirety.

In closing, it is to be understood that the embodiments disclosed herein are for illustrative purposes. Other modifications may be employed and are within the scope of the claims. Thus, by way of example, but not of limitation, alternative configurations may be utilized in accordance with the teachings herein. Accordingly, the teachings herein are not limited to that precisely as shown and described.

We claim:

1. A method of forming an elastomeric article of manufacture comprising;
   a. providing polymers having a general structure of formula 1, wherein the polymer comprises at least one pendent vinyl group,

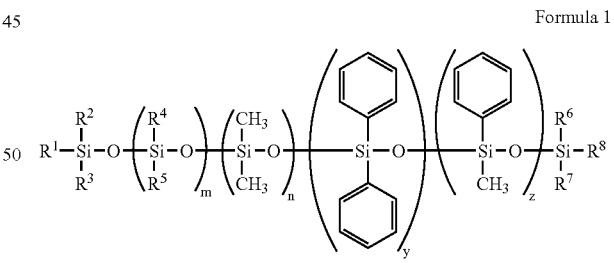

Formula 1 wherein the sum of m and n is x, x ranges from 0 to about 12000, y ranges from 0 to about 500, and z ranges from 0 to about 500, the sum of x, y, and z is at least 1, $R^1$-$R^8$ are each independently $CH_3$, $C_6H_5$ or $CH=CH_2$, if m is greater than zero, at least one of $R^4$ or $R^5$ must be $CH=CH_2$, and wherein more than four of $R^1$, $R^2$, $R^3$, $R^6$, $R^7$, or $R^8$ are $CH=CH_2$;

b. providing a cross-linker selected from a nonpolymeric cross-linker or a hydride terminated polymeric cross-linker;

c. providing a catalyst;

d. combining said polymer, said cross-linker and said catalyst to form a polymeric mixture; and e. curing said polymeric mixture;

wherein at least a portion of said elastomeric article of manufacture is formed.

2. The method according to claim 1, wherein said article of manufacture is selected from the group consisting of intraocular lenses, contact lenses, ocular lenses, body augmentation implants, medical device coatings and breast implants.

3. The method according to claim 1, wherein said article of manufacture is capable of controlled release of a therapeutic agent.

4. The method according to claim 1, wherein the cross-linker is selected from the group consisting of phenyltris(dimethylsiloxy)silane, 1,1,3,3,-tetraisopropyldisiloxane, 1,1,3,3,-tetramethyldisiloxane, 1,1,4,4-tetramethyldisilethane, bis(dimethylsilyl)ethane, 1,1,3,3-tetramethyldisilazane, tetrakis(dimethylsiloxy)silane, hydride-terminated polyphony-(dimethylhydrosiloxy)siloxane, hydride terminated polydimethylsiloxane, and hydride terminated methylhydrosiloxane-phenylmethylsiloxane copolymer.

5. The method according to claim 1, wherein said polymer is hexavinyl terminated.

* * * * *